US010993644B2

United States Patent
Huiku et al.

(10) Patent No.: US 10,993,644 B2
(45) Date of Patent: May 4, 2021

(54) SPO2 SYSTEM AND METHOD (71) Applicant: General Electric Company, Schenectady, NY (US)

(72) Inventors: Matti Veli Tapani Huiku, Espoo (FI); Sakari Lamminmaki, Espoo (FI)

(73) Assignee: General Electric Company, Schenectady, NY (US)

( * ) Notice: Subject to any disclaimer, the term of this patent is extended or adjusted under 35 U.S.C. 154(b) by 325 days.

(21) Appl. No.: 16/229,362

(22) Filed: Dec. 21, 2018

(65) Prior Publication Data
US 2020/0196926 A1 Jun. 25, 2020

(51) Int. Cl.
*A61B 5/1455* (2006.01)
*A61B 5/00* (2006.01)

(52) U.S. Cl.
CPC ........ *A61B 5/14551* (2013.01); *A61B 5/6815* (2013.01); *A61B 5/6826* (2013.01); *A61B 2560/0209* (2013.01); *A61B 2560/0431* (2013.01)

(58) Field of Classification Search
CPC ..... A61B 5/1455; A61B 5/14551; A61B 5/72; A61B 2560/0209; A61B 2560/0431; A61B 5/6815; A61B 5/6826
See application file for complete search history.

(56) References Cited

U.S. PATENT DOCUMENTS

| | | |
|---|---|---|
| 5,355,882 A | 10/1994 | Ukawa et al. |
| 5,697,374 A | 12/1997 | Odagiri et al. |
| 5,924,979 A * | 7/1999 | Swedlow ........... A61B 5/14551 600/323 |

(Continued)

FOREIGN PATENT DOCUMENTS

| | | |
|---|---|---|
| EP | 2832289 | 4/2015 |
| WO | 2005089640 | 9/2005 |

OTHER PUBLICATIONS

Lee et al., "Reflectance pulse oximetry: Practical issues and limitations", The Korean Institute of Communications Information Sciences, 2016, 195-198.

*Primary Examiner* — Eric F Winakur
(74) *Attorney, Agent, or Firm* — Andrus Intellectual Property Law, LLP (57) ABSTRACT

A $SpO_2$ measurement system includes at least one light transmitter configured to transmit a first wavelength light and a second wavelength light into tissue of a patient, wherein the second wavelength is shorter than the first wavelength, and a detection device that detects the first wavelength light and the second wavelength light emitted from the tissue of the patient. The $SpO_2$ measurement system operates the at least one light transmitter in a high power mode during a first time period to determine a $SpO_2$ value and a high power DC ratio based on the first wavelength light and the second wavelength light detected during operation in the high power mode. The $SpO_2$ measurement operates the at least one light transmitter in a low power mode during a second time period to determine a low power DC ratio based on the first wavelength light and the second wavelength light detected during operation in the low power mode, and to determine a blood oxygenation status for the patient based on the low power DC ratio.

20 Claims, 7 Drawing Sheets

(56) References Cited

U.S. PATENT DOCUMENTS

| | | |
|---|---|---|
| 6,151,107 A | 11/2000 | Schollermann et al. |
| 6,697,655 B2 | 2/2004 | Sueppel et al. |
| 6,697,658 B2 | 2/2004 | Al-Ali |
| 6,863,652 B2 | 3/2005 | Huang et al. |
| 6,912,413 B2 | 6/2005 | Rantala et al. |
| 6,987,994 B1 | 1/2006 | Mortz |
| 7,162,288 B2 | 1/2007 | Nordstrom et al. |
| 7,382,247 B2 | 6/2008 | Welch et al. |
| 8,515,509 B2 | 8/2013 | Bruinsma et al. |
| 8,571,622 B2 | 10/2013 | Huiku et al. |
| 9,072,439 B2 * | 7/2015 | Kassim ............... A61B 5/14551 |
| 9,237,855 B2 | 1/2016 | Hong et al. |
| 9,351,688 B2 * | 5/2016 | Iyer ..................... A61B 5/14552 |
| 10,188,330 B1 * | 1/2019 | Kadlec ............... A61B 5/14552 |
| 10,582,887 B2 * | 3/2020 | O'Donnell ......... A61B 5/14552 |
| 2009/0247849 A1 * | 10/2009 | McCutcheon ..... A61B 5/14551 |
| | | 600/323 |
| 2011/0029247 A1 * | 2/2011 | Kalathil ............... A61B 5/1455 |
| | | 702/19 |
| 2012/0053432 A1 | 3/2012 | Huiku et al. |
| 2014/0213912 A1 | 7/2014 | Su |
| 2015/0190078 A1 | 7/2015 | Lisogurski |
| 2015/0199485 A1 | 7/2015 | Borges |
| 2015/0289791 A1 | 10/2015 | Marcus |
| 2016/0143566 A1 * | 5/2016 | Ballam ............... A61B 5/14552 |
| | | 600/324 |

\* cited by examiner

SPO2 SYSTEM AND METHOD

BACKGROUND

This invention generally relates to pulse oximeters that non-invasively measure the oxygen saturation of hemoglobin arterial blood, and more specifically to systems and methods for measurement of $SpO_2$ that utilize a reduced power consumption.

Pulse oximetry is a well-established technique for measuring oxygen saturation ($SpO_2$) in arterial blood. $SpO_2$ is an important parameter, nowadays often called the fourth vital sign, which relates to the adequacy of oxygen supply to peripheral tissues and organs. Pulse oximeters provide instantaneous in-vivo measurements of arterial oxygenation, and thereby an early warning of arterial hypoxemia, for example. Pulse oximeters also display a photoplethysmographic (PPG) pulse waveform, which can be related to tissue blood volume and blood flow, i.e. the blood circulation at the site of the measurement, which is typically at the finger or ear. At present, there is a growing interest to develop portable and wearable medical sensors for various medical applications that allow the subject to move freely and thus also remote supervision of the subject. Wireless Body Area Network (WBAN) refers to short-range radio-frequency communications technologies, which are specifically suited for transmitting measurement data between different patient-worn devices. This includes battery-operated $SpO_2$ sensors.

Pulse oximetry typically uses two different light sources and a detection device, such as a photodiode. Two different measurement techniques are generally employed for measuring $SpO_2$, which include transmissive measurement technique where the light travels through the measurement site and is received on an opposite side of the measurement site, and a reflective measurement technique where the sensed light reflects off of the patient's tissue at the measurement site and is received by a detection device on the same side of the measurement site as the light source. Thus, transmissive measurement sensors have a light source on an opposite side of the measurement site from the detector. For reflective $SpO_2$ measurement, on the other hand, the light source and the detector are on the same side of the measurement site, and the light is reflected back at the detector by the tissue around the measurement site.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an $SpO_2$ measurement system includes at least one light transmitter configured to transmit light of at least a first wavelength and a second wavelength into tissue of a patient, wherein the second wavelength is shorter than the first wavelength, and a detection device configured to detect the first wavelength light and the second wavelength light emitted from the tissue of the patient. The $SpO_2$ measurement system is configured to operate in a high power mode during a first time period to determine a $SpO_2$ value and a high power DC ratio based on the detected first wavelength light and the detected second wavelength light. The $SpO_2$ measurement is further configured to operate in a low power mode during a second time period to determine a low power DC ratio based on the detected first wavelength light and the detected second wavelength light, and to determine a blood oxygenation status for the patient based on the low power DC ratio.

In one embodiment, a method of $SpO_2$ monitoring for a patient includes operating at least one light transmitter in a high power mode to transmit light of at least a first wavelength and a second wavelength into tissue of a patient, wherein the second wavelength is shorter than the first wavelength. The first wavelength light and the second wavelength light emitted from the tissue of the patient are detected. An $SpO_2$ value and a high power DC ratio are determined based on the detected first wavelength light and second wavelength light, wherein the high power DC ratio is a relationship between a first high power DC component of the detected first wavelength light and a second high power DC component of the detected second wavelength light detected while the light transmitter is operated in a high power mode. The light transmitter is then operated in a low power mode during a second time period to transmit the first wavelength light and the second wavelength light, and the first and second wavelength lights emitted from the tissue are then detected at a detection device. A low power DC ratio is then determined based on the detected first wavelength light and second wavelength light, wherein the low power DC ratio is a relationship between a low power DC component of the detected first wavelength light and a second low power DC component of the detected second wavelength light detected while the light transmitter is operated in the low power mode. A blood oxygenation status is then determined based on the low power DC ratio and the high power DC ratio.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Through their research and experience in the relevant field, the present inventors recognized that an improved SpO$_2$ sensor is needed that enables accurate SpO$_2$ measurement with relatively low power consumption. As wireless body worn devices operate on battery power and need to be relatively small and light so as not to impede patient movement or be uncomfortable, methods and systems are needed for reducing the power consumption of the LEDs generating light for the reflective or transmissive SpO$_2$ measurement. High powered light generation is generally necessary for conducting SpO$_2$ measurements, as the light needs to penetrate deeply into the tissue in order to pass through the necessary arteries and be received at the detector. This is especially true for in reflective SpO$_2$ sensors, where light must reflect back to the detector. Moreover, high sample rates are also necessary to adequately capture the changes in light alternation that occur with each pulse.

Thus, with currently available SpO$_2$ devices and systems, obtaining a reliable SpO$_2$ measurement requires a high-intensity light pulse and a high sampling rate for the light transmission and coordinated measurement. Generating that high-intensity light pulse at high frequency utilizes significant battery power. Additionally, many available SpO$_2$ devices utilize long light pulse lengths and high duty cycles to increase signal quality. This further increases the power consumption of the light transmitter and detector. Such high power consumption can be untenable for small battery-driven devices, such as wearable patient monitors, where significant size and weight constraints require small batteries.

Upon recognition of the foregoing problems and challenges, the present inventors developed the disclosed SpO$_2$ measurement system and methods that provide accurate SpO$_2$ measurement with a lower power consumption that utilize and track a DC component of the detected light signal that enables the SpO$_2$ measurement system to operate in a low power mode, such as operating the light transmitter LEDs at a minimum power level. The DC tracking can enable determination of a blood oxygen status for the patient, such as based on a comparison of the DC ratio obtained during the low power mode operation to a DC ratio obtained during a normal, high power mode of operation. In the low power mode of operation, the light transmitter is operated in a way that reduces its power consumption, such as by operating the light transmitter at a lower peak current, a shorter pulse length, a lower duty cycle, and/or a lower frequency than in the high power mode. Accordingly, the plethysmographic signal will likely be of low quality during the low power mode, which does not enable calculation of a reliable SpO$_2$ measurement. However, the inventors have recognized that the DC portion of the light pulse can be measured at a very low peak drive current of the LEDs, as well as utilizing a short pulse length and very low sampling frequency, since the DC component of the light level is a consistent value even when the plethysmographic pulse waveform is very noisy. When an extremely low sampling rate is used, such as one sample per second. At this low sampling rate, the plethysmographic pulse waveform or pulse rate cannot be extracted. However, sporadically switching back to high power mode will maintain sufficient patient safety even in case of compromised perfusion or cardiac arrhythmias.

Additionally, the inventors have recognized that by utilizing a relationship between the DC light levels of a first wavelength and a second wavelength, such as the red and infrared wavelengths typically used in SpO$_2$ monitoring, the DC ratio between the two wavelengths remains relatively constant, even when operating the LEDs at a significantly lower light intensity. Thus, the inventors recognized that the peak current utilized by the light transmitter could also be significantly reduced.

Specifically, the disclosed SpO$_2$ measurement system and method operates the light transmitter and detector in a high power mode during a first time period to determine a SpO$_2$ value and a high power DC ratio based on the DC components of two different wavelengths of light emitted from the tissue of the patient. The SpO$_2$ measurement system is then switched to a low power mode during a subsequent period of time, during which the light transmitter and detector are operated in power mode and a low power DC ratio is determined based on the DC aspects of the first and second wavelengths of light. Operation in the low power mode continues and the blood oxygen status for the patient is tracked based on the low power DC ratio. For example, the low power DC ratio may be compared to the high power DC ratio determined during operation in the high power mode. Since, as explained below, the DC component of the two wavelengths is influenced equivalently by changes in blood oxygenation in both the high and low power modes, the DC ratio can be utilized to track the blood oxygenation status of the patient and can be utilized as utilized as a proxy for the SpO$_2$ value.

Figure 1A:
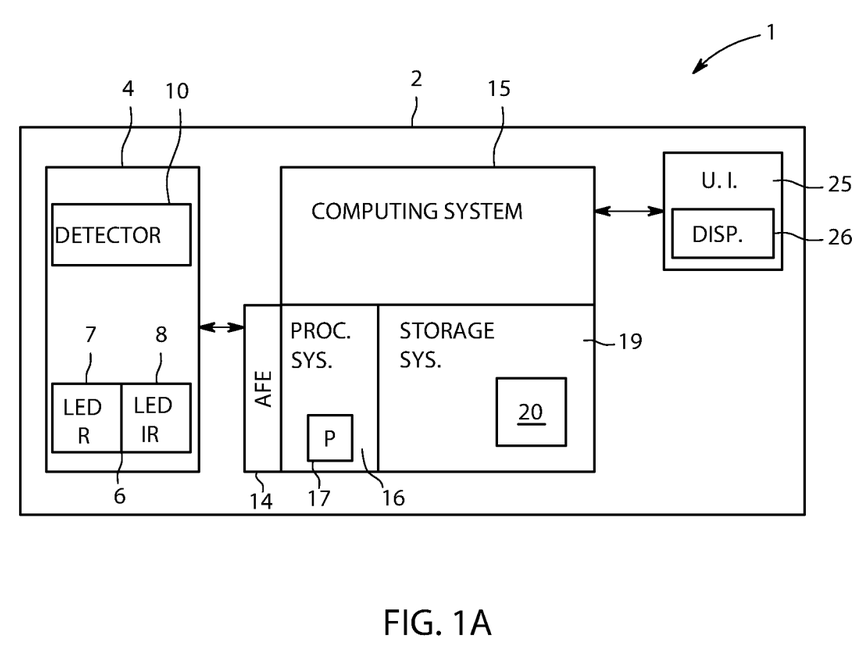
FIG. 1A schematically depicts an exemplary $SpO_2$ measurement system according to the present disclosure.

FIG. 1A depicts one embodiment of a SpO$_2$ measurement system 1 in accordance with the present disclosure. In the depicted embodiment, the SpO$_2$ measurement system 1 includes a SpO$_2$ monitor 2 having an optical probe device 4 that transmits and measures at least two wavelengths of light through the tissue of a patient. In various embodiments, the probe device may be configured as a transmissive measurement device or a reflective measurement device, and the methods and systems disclosed herein regarding utilization of the DC ratio for monitoring the blood oxygenation status in the low power mode can be applied in both a transmissive SpO$_2$ measurement system and a reflective SpO$_2$ measurement system.

The probe 4 communicates information, such as light measurement information, to the analog front end 14 and computing system 15. In the depicted embodiment, the computing system 15 comprises the SpO$_2$ control module 20, which is a set of software instructions stored within the computing system and executable by the processing system to carry out the methods and control functions described herein. The SpO$_2$ monitor 2 further includes a user interface 25 utilizable by an operator to provide input, such as to control the function and/or operation modes of the SpO$_2$ monitor. The user interface 25 may include a display 26 to display information to an operator, such as to display a calculated SpO$_2$ value or DC ratio value and/or to display blood oxygenation status information about the patient. In certain embodiments, the display 26 may also provide input function, such as by incorporating a touchscreen system.

The probe 4 includes at least one detection device 10 and at least one light transmitter 6. The light transmitter 6 is configured to transmit at least two different wavelengths of light into the tissue of a patient, wherein the second wavelength of light is shorter than the first wavelength. The light transmitter 6 includes one or more light sources appropriate for generating the at least two wavelengths required for SpO$_2$ measurement. In certain embodiments, each light source 7, 8 is comprised of one or more sets of LEDs. For example, the light transmitter 6 may include at least a red light source 7, such as a red LED (e.g., 660 nm), and an infrared light source 8, such as an infrared (IR) LED (e.g., 900 nm). In certain embodiments, the first or second light source may instead be an LED in the spectrum used for visible or near infrared spectroscopy (NIR) (e.g. ranging from 600 to 1100 nm), and no red or IR light source may be provided. In multi-wavelength applications, such as measurement of carboxyhemoglobin or methemoglobin or total hemoglobin, multiple (for example, eight) light sources of visible or NIR wavelengths can be used.

Figure 1B:
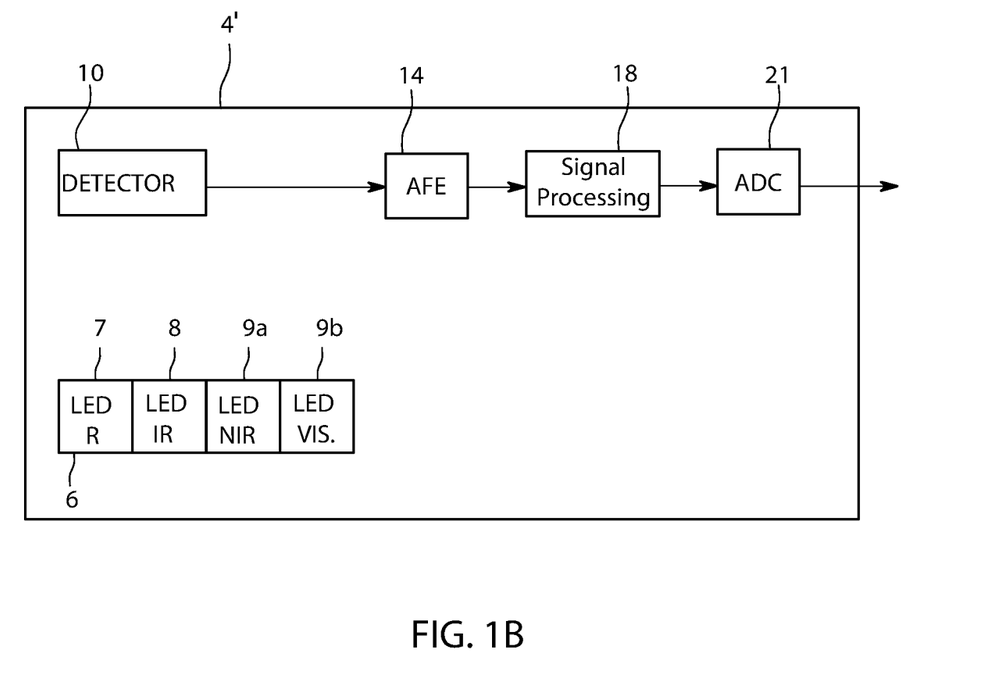
FIG. 1B schematically depicts another exemplary embodiment of a probe for measuring $SpO_2$ in accordance with one embodiment of the disclosure.

FIG. 1B schematically depicts another embodiment of a probe 4' including more than two light sources, which is shown as four light sources 7, 8, 9a, 9b, but may be more than four light sources (e.g., six or eight light sources). The depicted embodiment includes at least one NIR light source 9a (e.g., 690 nm, 760 nm, and/or 805 nm), and at least one additional visible-range light source 9b (e.g., 612 nm, 632 nm, and/or 660 nm). The LED sets may be configured such that the lumen output of the LEDs is controlled via dynamic current scaling, where a higher current is provided to the LEDs in order to emit a high-intensity light pulse, and a lower current is provided to the LEDs in order to lower the intensity of the emitted light pulse. Alternatively or additionally to lowering the peak current to LEDs, the low power mode may be activated by decreasing the LED current pulse length or current pulse frequency, thereby significantly changing the duty cycle of the light sources.

Each light source 7, 8 emits a respective wavelength of light, which may be at various intensities as is described above. While only one light source 7, 8 is operated at a time to emit its respective wavelength, the emissions are toggled at a fast enough frequency such that variation in measurement due to a physical change in the measurement area over time is not a factor. Typically the light sources are operated in pulse pairs timewise close to each other at repetition frequency of the pairs of several hundred Hz, much higher frequency than the cardiac cycle. The detector 10 is then operated in correspondence with the light sources 7 and 8 to scan the respective frequencies in sequence—e.g., red, infrared, red, infrared, etc. For example, the detector 10 may comprise one or more photodiodes positioned and configured to receive the respective wavelengths in accordance with their emission by the light transmitter 6. As mentioned above, this transmission receipt sequence is repeated at a high frequency, for example, at a sampling frequency of 100 Hz. Each wavelength has differing properties regarding how it scatters and is transmitted through tissue. The shorter wavelength, such as red wavelength or shorter, are more readily reflected by the tissue than the longer wavelength, such as infrared wavelengths. Conversely, the longer wavelengths are transmitted through tissue and human cells more easily.

In the depicted embodiment, the $SpO_2$ monitor 2 comprises a computing system 15 having a processing system 16 and analog front end 14 and a storage system 19 housing the $SpO_2$ control module 20. In various embodiments, the probe device 4, 4', signal processing system 16, computing system 15, and user interface 25 may be housed within a single housing, or may be separated into two or more separate housings. For example, the probe device 4, 4' may be housed in a probe housing configured for a transmission and detection of light at a particular measurement site, such as for conducting transmissive light wavelength measurements on a patient's finger. The computing system 15 may be housed, for example, in a hub device worn on or placed near the patient, and communication between the probe 4, 4' and signal processing devices 16, 18 and the computing system 15 in the hub may be provided by wireless or wired means. In such an embodiment, certain processing and communication control electronics may be provided within the probe device 4, 4' housing, such as to control the operation of the light transmitter 6 and detection device 10 in accordance with control instructions form the computing system 15, and may also provide digitization and/or certain signal processing functionality within the probe device 4, 4' housing. Accordingly, in certain embodiments, the $SpO_2$ control module 20 instructions and functionality may be divided across two separate device housings, and in such an embodiment the computing system 15 may incorporate one or more processing systems and storage systems distributed across two or more device housings.

FIG. 1B is a schematic diagram depicting the probe device 4' having an analog signal processing unit 18 and analog-to-digital converter 21, which communicates processed and digitized detector information. In embodiments where the probe device 4, 4' and computing system 15 are provided in separate devices, the probe device 4, 4' and computing system 15 may be connected by wired or wireless communication means. For example, the probe device 4, 4' may communicate detected light information to the computing system 15 by wireless means, which in certain examples may be any one of Bluetooth, Bluetooth low energy (BLE), ANT, or ZigBee. The computing system 15 may communicate control instructions to the probe device 4, 4' by the same or different wireless protocol. In still other embodiments, the probe device 4, 4' and the computing system 15 may be body area network (BAN) devices, such as medical body area network (MBAN) devices, that operate as a wireless network of wearable or portable computing devices. Alternatively, the probe device, 4' and the computing system 15 may be configured to operate on a longer-range wireless network, such as a network operating on the wireless medical telemetry service (WMTS) spectrum or on a Wi-Fi-compliant wireless local area network (WLAN). In wireless embodiments, each of the probe device 4, 4' and the computing system 15 will incorporate or employ respective radio frequency antennas and/or transmitters, or transceivers, configured to operate in accordance with the respective protocol.

The processing system 16 may employ one or more processors 17 and a storage system 19 storing software. The processing system 16 loads and executes software from the storage system 19, including the $SpO_2$ control module 20, which is an application within the software. The $SpO_2$ control module 20 includes computer-readable instructions that direct the processing system 16 to operate as described in herein in further detail. Although the computing system 15 as depicted in FIG. 1A includes one storage system 19 encapsulating one $SpO_2$ control module 20, it should be understood that one or more software elements having one or more modules may provide the same operation, and that such software elements may be housed in separate device housings and executed by separate processors. Similarly, while the description, as provided herein, refers to a computing system 15 and a processing system 16, it is to be recognized that implementations of such systems can be performed using one or more processors, which may be communicatively connected, and such implementations are considered to be within the scope of the description.

The processing system 16 includes at least one processor 17, which may be a microprocessor, a general purpose central processing unit, an application-specific processor, a microcontroller, or any other type of logic-based device. The processing system 16 may also include circuitry that retrieves and executes software from storage system 19. Processing system 16 can be implemented within a single processing device but can also be distributed across multiple processing devices or sub-systems that cooperate in executing program instructions.

The storage system 19 can comprise any storage media, or group of storage media, readable by processing system 16, and capable of storing software. The storage system 19 can include volatile and non-volatile, removable and non-removable media implemented in any method or technology for storage of information, such as computer-readable instructions, data structures, program modules, or other data. Storage system 19 can be implemented as a single storage device but may also be implemented across multiple storage devices or sub-systems. The storage media may be housed locally with the processing system 16, or may be distributed in one or more servers, which may be at multiple locations and networked, such as in cloud computing applications and systems.

The user interface 25 is configured to receive input from an operator, such as a clinician, and to display information relevant to the patient's $SpO_2$ or other blood oxygenation status indicator. User interface 25 includes a display, and may further include input devices such as a mouse, a keyboard, a voice input device, a touch input device for receiving a gesture from a user, a motion input device for detecting non-touch gestures and other motions by a user, and other comparable input devices and associated processing elements capable of receiving input from an operator user, such as a clinician. The user interface further includes a display 26, such as a video display or graphical display can display an interface further associated with embodiments of the system and method as disclosed herein. Speakers, printers, haptic devices and other types of output devices may also be included in the user interface 25.

Figure 2A:
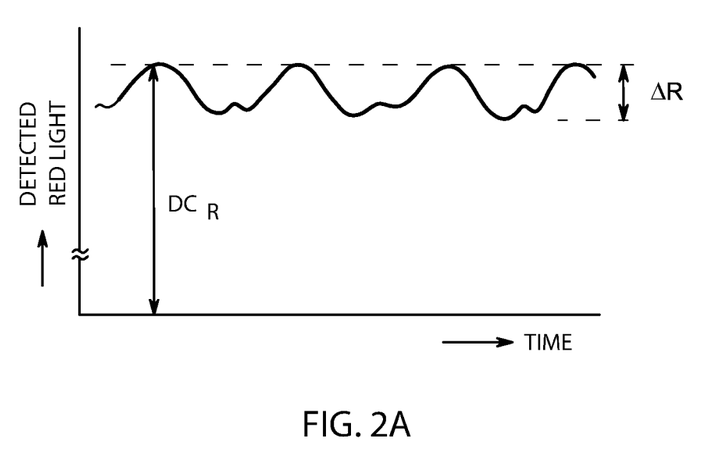
FIG. 2A is a graph illustrating the DC and pulsating components of a detected first wavelength of light in a $SpO_2$ monitor.
Figure 2B:
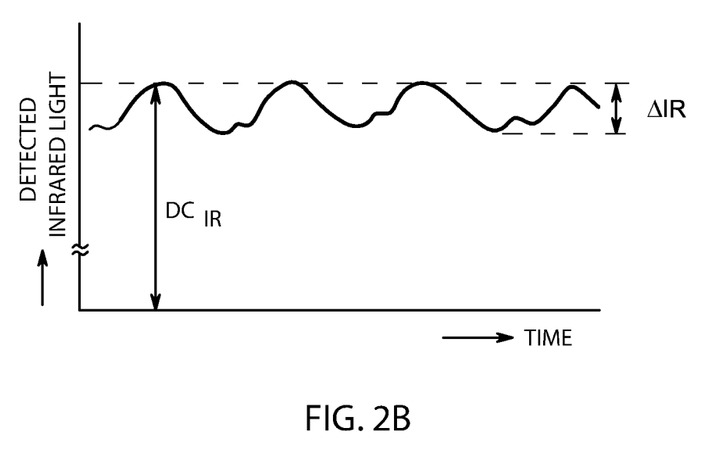
FIG. 2B is a graph illustrating DC and pulsating components of a second detected wavelength of light in a $SpO_2$ monitor.

FIGS. 2A and 2B are graphs showing the waveforms of the DC and pulsating components for first and second wavelengths of light. FIG. 2A represents detected red light received by the detection device 10. The DC component of the detected red light is representing as $DC_R$ and the pulsating component is represented as $\Delta_R$. The graph at FIG. 2B depicts the waveforms of the DC and pulsating components received at the detection device 10 for infrared light. The DC component of the detected IR wavelength light is represented as $DC_{IR}$, and the pulsating component of the IR wavelength light is represented as $\Delta_{IR}$.

The graphs at FIGS. 2A and 2B generally represent the detected light in the high power mode, where both the DC and pulsating components are detectable, such as where the strength of the emitted light and the sample rate are sufficient such that the pulsating component can be accurately measured. However, in certain embodiments of the low power mode, only the $DC_R$ and $DC_{IR}$ components may be measurable. For example, where the sampling frequency is too low, the pulsating component may not be accurately measurable. For example, a sample frequency of less than 10 Hz (i.e. where the light emitter and detector are operated to conduct less than 10 samples per second), the pulsating waveform may not be accurately measurable. In such an embodiment, only the DC components of the two different wavelength light ($DC_R$ and $DC_{IR}$) may be measured.

As will be known to a person having ordinary skill in the art, both of the pulsating and DC components of the detected light waveforms are necessary for the computation of a $SpO_2$ value. In the high power mode, both the DC and pulsating components can be measured, and thus the $SpO_2$ can be calculated. However, in the low power mode only the DC components may be measurable, which are relatively steady quantities of red and infrared light emerging from the tissue. In certain embodiments of the low power mode, especially where a lower intensity of light is utilized (e.g., a lower peak drive current for the LEDs), the DC components $DC_R$ and $DC_{IR}$ may decrease in magnitude. However, the inventors have recognized that the ratio between the DC components of the respective waveforms (e.g., $DC_R/DC_{IR}$) remains equivalent in both the low power and high power modes. Accordingly, a baseline, or calibrated, DC ratio can be calculated in the high power mode, when $SpO_2$ is also determined, and can be utilized for tracking the DC ratio in the low power mode. For example, assuming that the $SpO_2$ taken during the high power mode is within a normal or acceptable range, then a corresponding DC ratio can be calculated and used as a calibrated, reliable measurement for tracking the blood oxygenation status during operation in the low power mode.

For example, the DC ratio calculated based on $DC_R$ and $DC_{IR}$ measurements in the low power mode—i.e., the low power DC ratio—can be compared to the DC ratio calculated based on measurements taken in the high power mode—i.e., the high power DC ratio—to determine whether the blood oxygenation status remains stable. In other embodiments, the low power DC ratio may be compared to a change threshold representing a threshold amount of change for the DC ratio that indicates a potential change in blood oxygenation status for the patient. Various exemplary methods for assessing and monitoring the blood oxygenation status based on the low power DC ratio are described herein.

Figure 3:
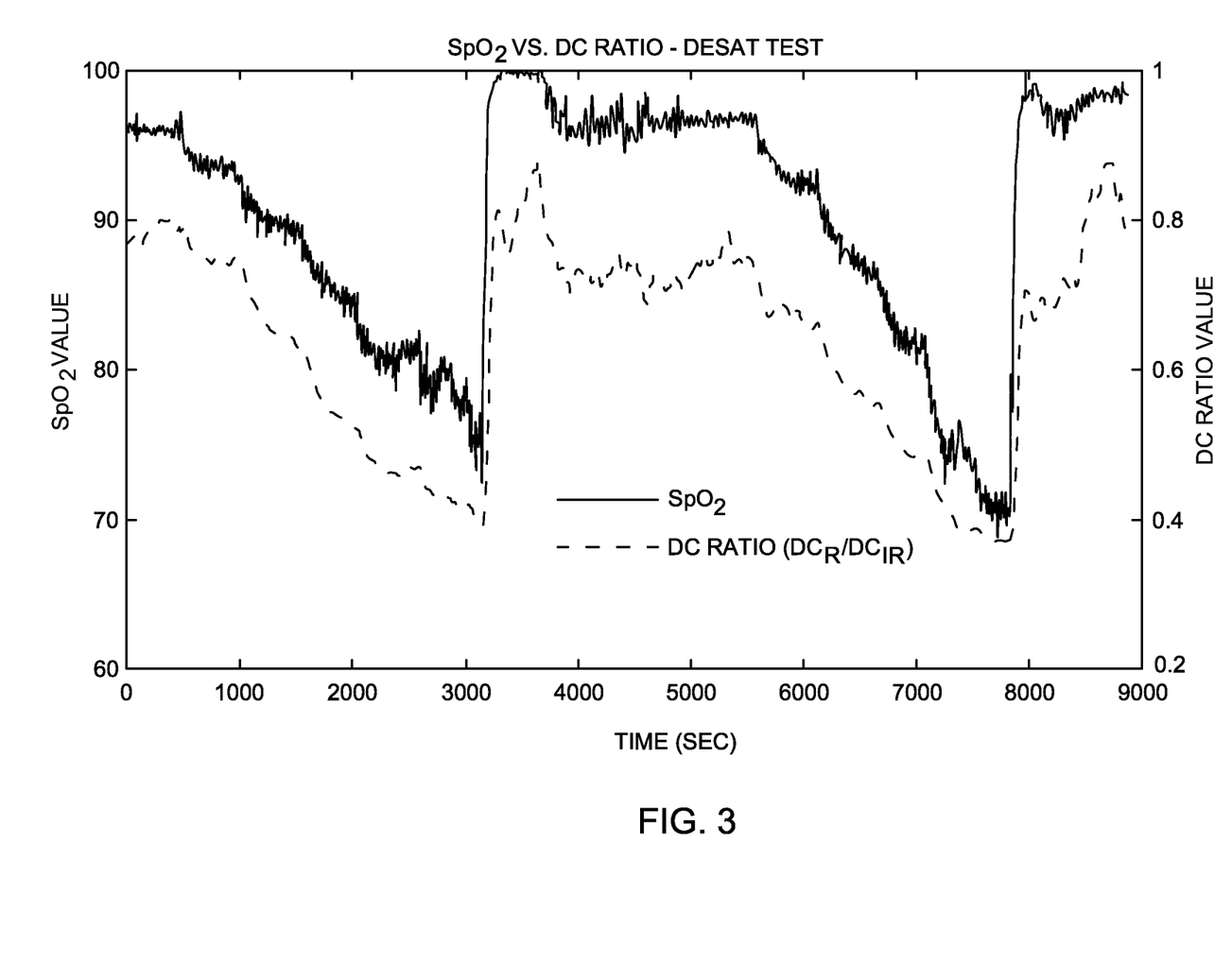
FIG. 3 is a graph showing an exemplary relationship between $SpO_2$ measurements and DC ratios for a patient over time.

FIG. 3 is a graph comparing the $SpO_2$ value and corresponding DC ratio value measured for the patient over time, such as in the high power mode. The left axis represents the $SpO_2$ axis and the right vertical axis represents the DC ratio value. As can be seen, the magnitude of fluctuation of the $SpO_2$ is significantly more than that of the DC ratio. In the depicted example the DC ratio fluctuates between approximately 0.4 and 0.8, while the $SpO_2$ value fluctuates approximately 70 and 100. However, the time and direction of the changes in $SpO_2$ value are mirrored by changes in the DC ratio value, illustrating that the DC ratio value is equally susceptible to changes in blood oxygenation as the AC ratio. The actual value of the DC ratio may vary significantly between patients and is dependent on various factors, including skin pigmentation, and the type of sensor utilized to make the measurement.

While the DC ratio is subject to change based on blood oxygenation, and thus can be used to track the patient's blood oxygenation status, the DC ratio value is also susceptible to changes in blood volume. Thus, a change in the low power DC ratio could indicate that the patient's blood oxygenation status has deteriorated; however, false positives may occur where the blood volume at the measurement site changes, such as due to a change in the patient's activity or position. Accordingly, if a change is seen in the low power DC ratio, the $SpO_2$ measurement system 1 switches back to operating in the high power mode to determine an actual $SpO_2$ value, which is a more reliable measurement of blood oxygenation and can rule out measurement changes due to changes in blood volume.

In certain embodiments, the DC ratio determined in the low power mode may be tracked based on an established $SpO_2$/DC ratio relationship in the high power mode, which is a relationship between DC ratio values calculated for the patient and corresponding $SpO_2$ values calculated for the patient. As observed in FIG. 3 this relationship is not necessarily linear and, in addition, it varies considerably between patients. In certain embodiments, the established typical SpO$_2$/DC ratio relationship with non-linearity may be determined based on population data. For example, the population normal DC ratio and the SpO$_2$ values may be predetermined based on relationships between SpO$_2$ values and DC ratio values for data from a multitude of people, such as general population data or some subset of population data correlated based on the demographics of the particular patient being monitored.

Figure 4:
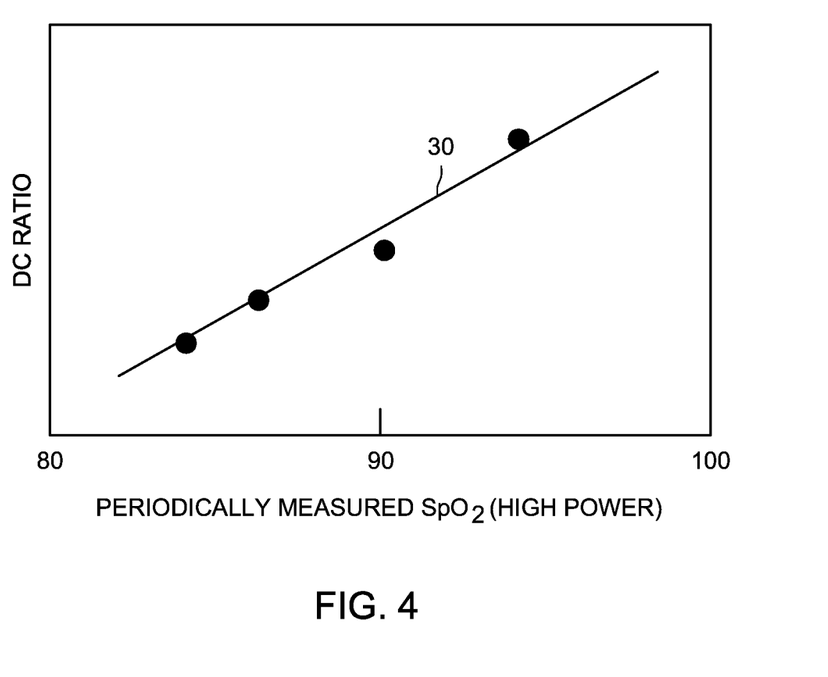
FIG. 4 is a graph showing an established $SpO_2$/DC ratio relationship based on acquired patient data.

The relationship can be determined within one patient as well, if the patient has big enough SpO2 changes during monitoring. This results in accurate individual calibration within this particular patient. Thus, once a baseline DC ratio is established for the patient, which has a corresponding baseline SpO$_2$ value, the established SpO$_2$/DC relationship can be determined based the individual data and the baseline measurement of the DC ratio and the SpO$_2$ value. In these embodiments, the established SpO$_2$/DC ratio relationship is thus a patient-specific relationship between previously determined high power DC ratios and corresponding SpO$_2$ values calculated for the patient. For example, once two or more differing SpO$_2$ values and corresponding DC ratios have been determined for the patient, the slope of the line connecting the values can be determined. FIG. 4 provides one such example, which contains four data points representing four different SpO$_2$ values and corresponding DC ratios measured in the high power mode. The line 30 is fit to the data points, and the slope of the line 30 represents the patient-specific established SpO$_2$/DC ratio relationship.

Since determining a patient-specific established SpO$_2$/DC ratio relationship requires measurement of at least two or more SpO$_2$ values for a patient, a patient-specific relationship may not be immediately determinable upon starting a patient monitoring session on a patient. Since patients' SpO$_2$ values often are relatively stable, it may take several minutes or hours of monitoring before sufficient data can be gathered from the patient to generate the patient-specific relationship. Therefore, in certain embodiments, the system 1 may be configured to initially generate the established SpO$_2$/DC ratio relationship based on population data and the high power DC ratio. That initial established SpO$_2$/DC ratio relationship can then be utilized until sufficient data exists to generate a patient-specific established SpO$_2$/DC ratio relationship.

In certain embodiments, the established SpO$_2$/DC ratio relationship can be utilized in the low power mode to approximate the SpO$_2$ for the patient based on the low power DC ratio. Alternatively or additionally, the established SpO$_2$/DC relationship can be utilized to determine a threshold change value for the low power DC ratio. For example, the threshold change value may be a change in the DC ratio corresponding to a predetermined change in the SpO$_2$ value, which can be calculated once the established SpO$_2$/DC relationship is determined.

Figure 5A:
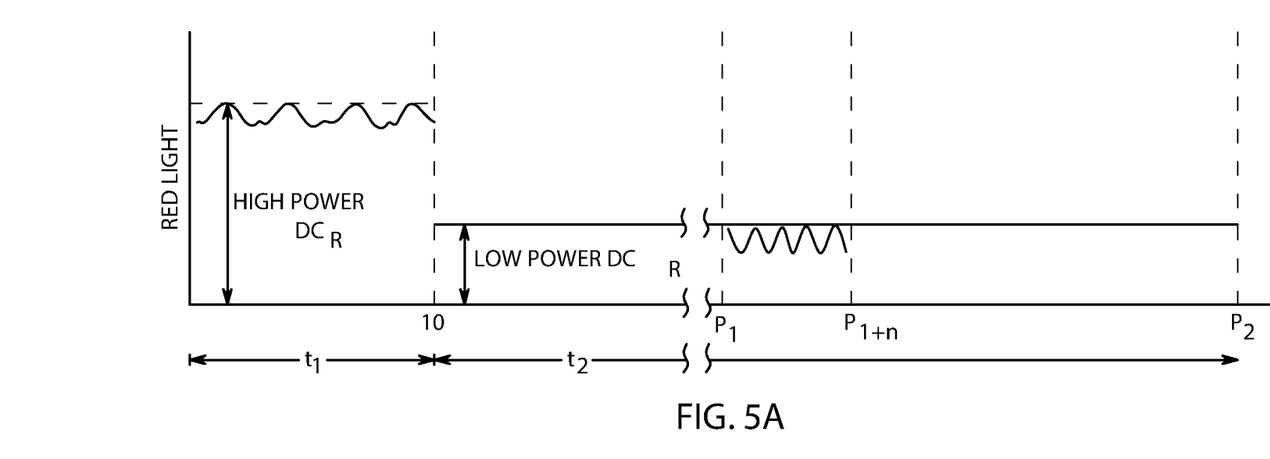
FIGS. 5A and 5B exemplify a method of $SpO_2$ monitoring and corresponding $SpO_2$ measurement system operation over exemplary first and second time periods, according to one embodiment of the present disclosure.
Figure 5B:
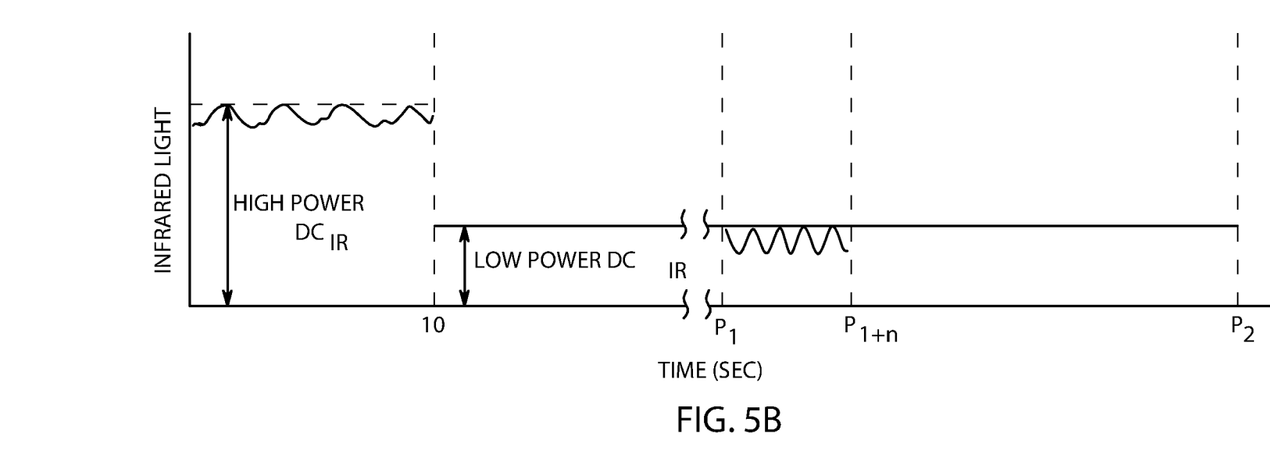

FIGS. 5A and 5B are graphs depicting measurements and exemplary operation in both the high power and low power modes. In the depicted example, the high power mode of operation occurs during a first time period $t_1$, where both the DC and pulsating components of the two different wavelengths of light are measured. One or more SpO$_2$ values are determined during the first time period $t_1$ based on the DC and pulsating component measurements. One or more high power DC ratios are also determined. Assuming that the SpO$_2$ value is stable and within the normal range for the patient, a baseline for the DC ratio is thus established based on the measurements made in the high power mode (i.e., the high power DC ratio). An established SpO$_2$/DC ratio relationship may also be determined, such as based on population SpO$_2$ data and the SpO$_2$ values and high power DC ratios. Once the baseline SpO$_2$ value and high power DC ratio are established during the first time period $t_1$, the SpO$_2$ measurement system 1 switches to operation in a low power mode during a second time period $t_2$. The switch from the high power mode to the low power mode may be conducted after a predetermined amount of time, which in the depicted example is a first time period $t_1$ of ten seconds. Alternatively or additionally, the switch to the low power mode can be based on the stability of the SpO$_2$ value and whether the SpO$_2$ value is within a normal range, indicating that the patient's blood oxygen status is normal.

As described above, in the low power mode the light transmitter 6 is operated with at least one of a lower peak current to drive the light transmission, a shorter pulse length, a lower duty cycle, and a lower sampling frequency than in the high power mode. Where a lower peak current is used, for example, the low power DC values for each of the wavelengths will be less than the corresponding high power DC values. FIG. 5A depicts the low power operation for the first wavelength of light, which in the depicted embodiment is red light, and FIG. 5B depicts operation and detection of a second wavelength of light, which in the depicted embodiment is infrared light. In the low power mode, only the DC value is measured and the pulsating component is not measured. In the depicted example, the low power $DC_R$ and $DC_{IR}$ values are less than the respective high power DC values because a lower peak current is utilized to drive the light transmitter.

The low power mode continues for the second time period $t_2$ which may be substantially longer than the first time period $t_1$. For example, assuming that the low power DC ratio remains stable, the second time period $t_2$ (e.g., the predetermined low power period $P_2$ of FIGS. 5A and 5B) may last several minutes, or even up to several hours. In certain embodiments, the SpO$_2$ measurement system 1 may be configured to remain in the low power mode tracking the low power DC ratio unless and until a threshold change is seen in the low power DC ratio. In other embodiments, the SpO$_2$ measurement system may be configured to stay in the low power mode for a second time period $t_2$, which may be a predetermined time period. The SpO$_2$ measurement system 1 may thus be configured to toggle between the high power mode for the first time period $t_1$ and the low power mode for the second time period $t_2$. In still other embodiments, the system 1 may be configured to exit the low power mode and resume the high power mode upon expiration of a predetermined second time period $t_2$, or upon detection of a threshold change in the low power DC ratio, whichever occurs first.

In certain embodiments, the low power mode may be configured such that, in addition to the low power DC value, a pulse rate is also measured from the patient. For example, the peak current, pulse length, duty cycle, and sampling frequency may be lower than that of the high power mode, but still high enough such that a pulse rate can be measured. In many applications, a sampling frequency of at least 10 Hz must be maintained in order to obtain a reliable pulse rate from the detected wavelength measurements.

In certain embodiments, the SpO$_2$ measurement system 1 may be configured to vary its operation while in the low power mode to operate for periods of time where only the DC ratio is determined, and thus the light transmitter 6 is operated such that only a minimal amount of power is consumed. In certain embodiments, during the low power mode operation, operation of the light transmitter 6 and the detection device 10 may be adjusted, such as by increasing the sampling frequency from below 10 Hz to above 10 Hz, to enable determination of a pulse rate. Thus, the power consumption by the probe device 4, 4' may be increased slightly during the low power mode of operation to determine a pulse rate, which is still significantly less than the power consumption by the probe device 4, 4' operating in the high power mode. For example, the system may be configured to periodically determine pulse rate during low power mode operation, such as for a predetermined amount of time, and thus to periodically increase the power consumption of operation while still remaining in the low power mode. After the periodic pulse rate measurement, the probe device 4, 4' may be returned to the lowest power consumption where only the DC components of the detected light are measured.

Further, in certain other embodiments, the sampling rate of the detector signal is lowered only for one channel, such as lowered in the red wavelength channel and maintained high for the IR channel. This embodiment allows accurate pulse rate and plethysmographic measurement, still lowering the power consumption considerably. In certain embodiments, during the operation in the high power mode as well as in the low power mode, the sampling frequency of the detector signal can be selected so that the signal quality is optimal. Such a situation may occur when ambient light interference is present and disturbs the plethysmographic measurement. As the ambient light interference is dependent on the ambient light frequency spectrum, it is advantageous to select the sampling frequency at the portion of the spectrum where the ambient light power is the least. At these sampling frequencies the LED intensities can be lowered without compromising the plethysmographic waveform measurements.

In the depicted example, the low power mode of operation during the second time period $t_2$ includes, after a predetermined period of time $P_1$, increasing the sampling frequency slightly so that the pulse rate of the patient is obtained, where the sampling rate is increased sufficiently to enable extraction of the plethysmographic pulse wave. The increased sampling frequency is maintained for a period of time (until $P_1+n$), which is an amount of time sufficient for measurement and display of the plethysmographic pulse wave, such as for verification that the waveform is normal (e.g., no cardiac arrhythmias are present). Assuming that the pulse rate and the low power DC ratio are acceptable, the low power mode of operation continues until expiration of the predetermined low power period $P_2$. After the expiration of the predetermined low power period $P_2$, the $SpO_2$ measurement system 1 switches to the high power mode of operation to check the $SpO_2$ value and recalibrate the DC ratio based on the high power measurements.

Similarly, in certain embodiments, the $SpO_2$ measurement system 1 may be configured to have three or more power modes of operation, including at least high and low power modes as described above, as well as a medium power mode that consumes a power amount between the high power mode and the low power mode. For example, the $SpO_2$ measurement system 1 may be configured to select between the low power mode and the medium power mode based on one or both of the patient status—whether the patient's condition has a significant likelihood of deteriorating—and a charge status of the battery.

Accordingly, significant power savings can be obtained by operating the $SpO_2$ measurement system in the low power mode for the majority of the operation time, especially during time periods where the patient's blood oxygen status is normal and consistent.

Figure 6:
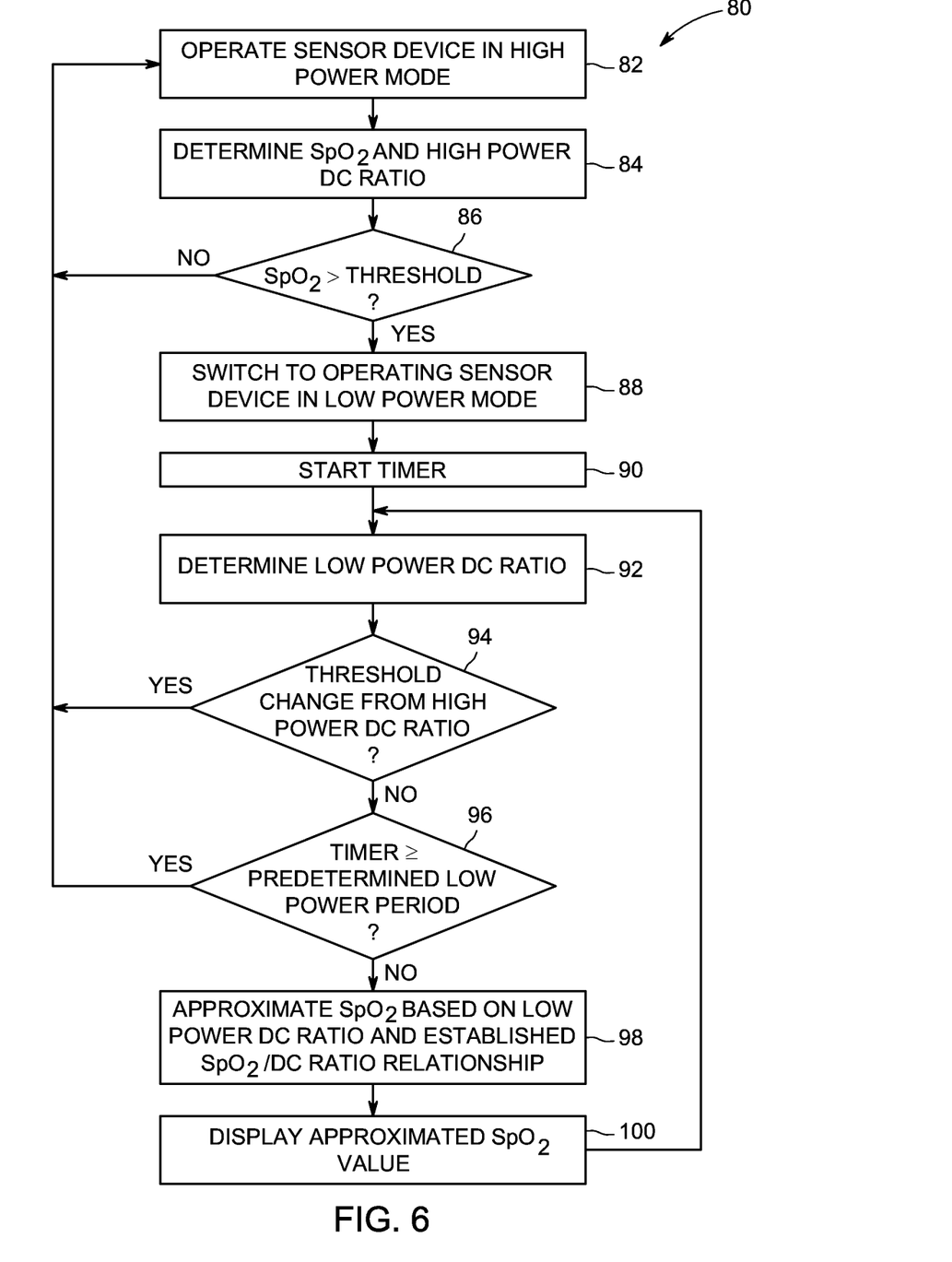
FIG. 6 is a flowchart exemplifying one method of $SpO_2$ monitoring according to the present disclosure.

FIG. 6 is a flow chart depicting an exemplary method 80 of $SpO_2$ monitoring involving the low power mode DC tracking described above. For example, the steps represented in FIG. 6 may be executed by the $SpO_2$ control module 20 controlling and receiving detected information from the probe device 4, 4'. At step 82, the probe device is operated in high power mode, including operating the light transmitter 6 and the detection device 10 to transmit and detect the first and second wavelengths of light in the high power mode. A $SpO_2$ value and high power DC ratio are determined at step 84. Step 86 is executed to determine whether the $SpO_2$ exceeds an acceptable threshold, such as a threshold for a normal patient $SpO_2$ value or stability of the SpO2 reading. If the $SpO_2$ value is less than the threshold, then the probe device 4, 4' continues to be operated in the high power mode until the $SpO_2$ measurement exceeds the threshold at step 86. In certain embodiments, a consistency requirement may also be set, such that the $SpO_2$ value exceeds the acceptability threshold for at least a predetermined period of time. Once the consistency threshold is met, and thus a baseline $SpO_2$ and DC ratio are established, the probe device 4, 4' is switched to operation in the low power mode at step 88. For example, the light transmitter 6 may be operated with at least one of a lower peak current, a shorter pulse length, a lower duty cycle, and/or a lower sampling frequency. In certain embodiments, step 86 can be omitted and the transition to the step 88 may be made without threshold criteria. The detection device 10 is correspondingly operated to detect the light transmitted through the patient's tissue.

Upon initiation of the low power mode, a timer is started at step 90. The low power DC ratio is determined at step 92, such as a ratio of the measured DC value of the detected red light to the measured DC value of the detected infrared light. In the depicted exemplary method, the low power DC ratio is compared to the high power DC ratio to determine a difference between the values representing a change in the DC ratio. If a threshold change in the DC ratio is exhibited at step 94, then the probe device 4, 4' is switched back to operation in the high power mode so that a $SpO_2$ can be determined. If the DC ratio remains consistent at step 94, and the timer has not reached the predetermined low power period at step 96, then step 98 is executed to determine an estimated $SpO_2$ from the low power DC ratio utilizing the established $SpO_2$/DC ratio relationship. The approximate $SpO_2$ value is then displayed at step 100, thereby indicating the blood oxygenation status of the patient. In other embodiments, the blood oxygenation status may be indicated by other means. For example, a blood oxygenation indicator may be utilized, such as to indicate that the blood oxygenation status is either acceptable or unacceptable based on the DC ratio. In other embodiments, an indicator of the low power DC ratio itself may be depicted, such as a graph or other image showing the low power DC ratio over time, or how the low power DC ratio compares to the high power DC ratio.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A SpO2 measurement system comprising:
   at least one light transmitter configured to transmit at least a first wavelength light and a second wavelength light into tissue of a patient, wherein the second wavelength is shorter than the first wavelength;
   a detection device configured to detect the first wavelength light and the second wavelength light emitted from the tissue of the patient;
   wherein the SpO2 measurement system is configured to operate the at least one light transmitter in a high power mode during a first time period, and to determine a SpO2 value and a high power DC ratio based on the first wavelength light and the second wavelength light detected during operation in the high power mode; and
   wherein the SpO2 measurement system is configured to operate the at least one light transmitter in a low power mode during a second time period, and to determine a low power DC ratio based on the first wavelength light and the second wavelength light detected during operation in the low power mode, and to determine a blood oxygenation status for the patient during operation in the low power mode based on the low power DC ratio.

2. The system of claim 1, wherein in the low power mode, the at least one light transmitter is operated with at least one of a lower peak current, a shorter pulse length, a lower duty cycle, and a lower sampling frequency than in the high power mode.

3. The system of claim 2, wherein the at least one light transmitter and the detection device are operated in the high power mode at a sampling frequency greater than 100 Hz, and wherein the at least one light transmitter and the detection device are operated in the low power mode at a sampling frequency less than 10 Hz.

4. The system of claim 2, wherein the lower sampling frequency is assigned at a spectrum portion where ambient light power is minimized so as to minimize ambient light interference.

5. The system of claim 1, wherein in the low power mode, the SpO2 measurement system is configured to determine the blood oxygenation status based on a difference between the high power DC ratio determined during operation in the high power mode and the low power DC ratio.

6. The system of claim 1, the SpO2 measurement system is configured to determine a change in the low power DC ratio during operation in the low power mode, and to determine the blood oxygenation status based on the change in the low power DC ratio.

7. The system of claim 6, wherein in the low power mode, the SpO2 measurement system is further configured to:
   compare the change in the low power DC ratio to a threshold change value; and
   wherein the blood oxygenation status is determined based on the comparison.

8. The system of claim 7, wherein the SpO2 measurement system is further configured to switch from operating in the low power mode back to operating in the high power mode if the change in the low power DC ratio exceeds the threshold change value, or upon expiration of a predetermined low power period, whichever occurs first.

9. The system of claim 1, wherein in the low power mode, the SpO2 measurement system is further configured to determine an estimated SpO2 based on the low power DC ratio and an established SpO2/DC ratio relationship.

10. The system of claim 9, wherein the established SpO2/DC ratio relationship is based on the high power DC ratio and population data, or wherein the established SpO2/DC ratio relationship is a patient-specific relationship between previously determined high power DC ratios and corresponding SpO2 values for the patient.

11. A method of SpO2 monitoring of a patient, the method comprising:
    operating at least one light transmitter in a high power mode to transmit a first wavelength light and a second wavelength light into tissue of a patient, wherein the second wavelength is shorter than the first wavelength;
    detecting at least the first wavelength light and the second wavelength light emitted from the tissue of the patient;
    determining an SpO2 value and a high power DC ratio based on the detected first wavelength light and second wavelength light, wherein the high power DC ratio is a relationship between a high power DC component of the first wavelength light and a high power DC component of the second wavelength light detected while light transmitter is operated in the high power mode;
    operating the at least one light transmitter in a low power mode during a second time period to transmit the first wavelength light and the second wavelength light;
    detecting the first wavelength light and the second wavelength light emitted from the tissue of the patient;
    determining a low power DC ratio based on the detected first wavelength light and second wavelength light, wherein the low power DC ratio is a relationship between a low power DC component of the first wavelength light and a low power DC component of the second wavelength light detected while light transmitter is operated in the low power mode; and
    determining a blood oxygenation status based on the low power DC ratio.

12. The method of claim 11, wherein the at least one light transmitter is operated in the low power mode with at least one of a lower peak current, a shorter pulse length, a lower duty cycle, and a lower sampling frequency than in the high power mode.

13. The method of claim 12, wherein the at least one light transmitter and the detection device are operated in the high power mode at a sampling frequency greater than 100 Hz, and wherein the at least one light transmitter and the detection device are operated in the low power mode at a sampling frequency less than 10 Hz.

14. The method of claim 11, further comprising determining the blood oxygenation status based on a difference between the low power DC ratio and the high power DC ratio determined during operation in the high power mode.

15. The method of claim 11, further comprising:
    determining a change in the low power DC ratio;
    comparing the change in the low power DC ratio to a threshold change value, wherein the threshold change value is based on the high power DC ratio; and
    wherein the blood oxygenation status is determined based on the comparison.

16. The method of claim 15, further comprising switching from operating in the low power mode back to operating in the high power mode if the change in the low power DC ratio exceeds the threshold change value, or upon expiration of a predetermined low power period, whichever occurs first.

17. The method of claim 15, further comprising determining the threshold change value based on the high power DC ratio and an established SpO2/DC ratio relationship.

18. The method of claim 17, further comprising determining a patient-specific established SpO2/DC ratio relationship between previously-determined high power DC ratios and corresponding SpO2 values for the patient.

19. The method of claim 11, further comprising determining an estimated SpO2 based on the low power DC ratio and an established SpO2/DC ratio relationship.

20. The method of claim 19, wherein the established SpO2/DC ratio relationship is based on the high power DC ratio and population data, or wherein the established SpO2/DC ratio relationship is a patient-specific relationship between previously-determined high power DC ratios and SpO2 values for the patient.

* * * * *